(12) United States Patent
Surti et al.

(10) Patent No.: US 8,603,121 B2
(45) Date of Patent: Dec. 10, 2013

(54) SYSTEMS AND METHODS FOR CREATING ANASTOMOSES

(75) Inventors: Vihar C. Surti, Winston-Salem, NC (US); Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 250 days.

(21) Appl. No.: 13/086,097

(22) Filed: Apr. 13, 2011

(65) Prior Publication Data

US 2011/0257668 A1   Oct. 20, 2011

Related U.S. Application Data

(60) Provisional application No. 61/324,132, filed on Apr. 14, 2010.

(51) Int. Cl.
  *A61B 17/08* (2006.01)
(52) U.S. Cl.
  USPC .......................................................... 606/153
(58) Field of Classification Search
  USPC ......... 606/139, 142, 144, 153, 213, 215, 216, 606/232; 227/175.1; 128/898
  See application file for complete search history.

(56) References Cited

U.S. PATENT DOCUMENTS

| 1,783,484 A | 12/1930 | Ross |
| 3,057,028 A | 10/1962 | Lorber |
| 3,299,883 A | 1/1967 | Rubens |
| 3,358,676 A | 12/1967 | Frei et al. |
| 3,674,014 A | 7/1972 | Tillander |
| 3,709,214 A | 1/1973 | Robertson |
| 4,022,208 A | 5/1977 | Valtchev |
| 4,214,587 A | 7/1980 | Sakura, Jr. |
| 4,899,744 A | 2/1990 | Fujitsuka et al. |
| 5,081,997 A | 1/1992 | Bosley et al. |
| 5,234,447 A | 8/1993 | Kaster et al. |
| 5,297,536 A | 3/1994 | Wilk |

(Continued)

FOREIGN PATENT DOCUMENTS

| DE | 19704211 | 8/1998 |
| EP | 1077047 A2 | 2/2001 |

(Continued)

OTHER PUBLICATIONS

International Search Report and Written Opinion for PCT/US2011/032289 dated Jul. 25, 2011.

(Continued)

*Primary Examiner* — Julian W Woo
(74) *Attorney, Agent, or Firm* — Brinks Hofer Gilson & Lione

(57) ABSTRACT

Medical system and methods are provided for forming an Anastomosis, such as an intestinal bypass anastomosis for treatment of obesity or diabetes. The medical devices and methods are minimally invasive and reduce complications. One embodiment of the method includes forming a first opening in the first section and forming a second opening in the first section. A proximal portion of the second section is moved to a position adjacent the first opening, and a distal portion of the second section is moved to a position adjacent the second opening. In this manner, an intermediate portion of the second section extends along the first section and an anastomosis can then be formed between the first section and the second section.

19 Claims, 7 Drawing Sheets

(56) References Cited

U.S. PATENT DOCUMENTS

| | | |
|---|---|---|
| 5,346,501 A | 9/1994 | Regula et al. |
| 5,391,156 A | 2/1995 | Hildwein et al. |
| 5,429,131 A | 7/1995 | Scheinman et al. |
| 5,458,131 A | 10/1995 | Wilk |
| 5,554,183 A | 9/1996 | Nazari |
| 5,562,683 A | 10/1996 | Chan |
| 5,562,688 A | 10/1996 | Riza |
| 5,571,090 A | 11/1996 | Sherts |
| 5,571,119 A | 11/1996 | Atala |
| 5,573,540 A | 11/1996 | Yoon |
| 5,573,543 A | 11/1996 | Akopov et al. |
| 5,578,044 A | 11/1996 | Gordon et al. |
| 5,582,615 A | 12/1996 | Foshee et al. |
| 5,584,835 A | 12/1996 | Greenfield |
| 5,586,986 A | 12/1996 | Hinchcliffe |
| 5,593,414 A | 1/1997 | Shipp et al. |
| 5,630,824 A | 5/1997 | Hart |
| 5,643,292 A | 7/1997 | Hart |
| 5,643,317 A | 7/1997 | Pavcnik et al. |
| 5,645,552 A | 7/1997 | Sherts |
| 5,653,717 A | 8/1997 | Ko et al. |
| 5,665,067 A | 9/1997 | Linder et al. |
| 5,667,527 A | 9/1997 | Cook et al. |
| 5,674,231 A | 10/1997 | Green et al. |
| 5,683,402 A | 11/1997 | Cosgrove et al. |
| 5,690,656 A | 11/1997 | Cope et al. |
| 5,693,060 A | 12/1997 | Martin |
| 5,695,525 A | 12/1997 | Mulhauser et al. |
| 5,700,273 A | 12/1997 | Buelna et al. |
| 5,728,113 A | 3/1998 | Sherts |
| 5,728,116 A | 3/1998 | Rosenman |
| 5,741,278 A | 4/1998 | Stevens |
| 5,746,751 A | 5/1998 | Sherts |
| 5,779,720 A | 7/1998 | Walder-Utz et al. |
| 5,788,625 A | 8/1998 | Plouhar et al. |
| 5,792,153 A | 8/1998 | Swain et al. |
| 5,810,848 A | 9/1998 | Hayhurst |
| 5,824,010 A | 10/1998 | McDonald |
| 5,836,955 A | 11/1998 | Buelna et al. |
| 5,836,956 A | 11/1998 | Buelna et al. |
| 5,846,253 A | 12/1998 | Buelna et al. |
| 5,860,990 A | 1/1999 | Nobis et al. |
| 5,865,791 A | 2/1999 | Whayne et al. |
| 5,865,836 A | 2/1999 | Miller |
| 5,868,763 A | 2/1999 | Spence et al. |
| 5,873,530 A | 2/1999 | Chizinsky |
| 5,891,159 A | 4/1999 | Sherman et al. |
| 5,902,228 A | 5/1999 | Schulsinger et al. |
| 5,908,428 A | 6/1999 | Scirica et al. |
| 5,919,184 A | 7/1999 | Tilton, Jr. |
| 5,931,844 A | 8/1999 | Thompson et al. |
| 5,938,668 A | 8/1999 | Scirica et al. |
| 5,947,997 A | 9/1999 | Pavcnik et al. |
| 5,948,000 A | 9/1999 | Larsen et al. |
| 5,951,531 A | 9/1999 | Ferdman et al. |
| 5,968,078 A | 10/1999 | Grotz |
| 5,972,002 A | 10/1999 | Bark et al. |
| 5,976,159 A | 11/1999 | Bolduc et al. |
| 5,984,949 A | 11/1999 | Levin |
| 6,007,515 A | 12/1999 | Epstein et al. |
| 6,015,414 A | 1/2000 | Werp et al. |
| 6,021,776 A | 2/2000 | Allred et al. |
| 6,030,365 A | 2/2000 | Laufer |
| 6,059,749 A | 5/2000 | Marx |
| 6,077,217 A | 6/2000 | Love et al. |
| 6,086,608 A | 7/2000 | Ek et al. |
| 6,110,183 A | 8/2000 | Cope |
| 6,113,612 A | 9/2000 | Swanson et al. |
| 6,149,658 A | 11/2000 | Gardiner et al. |
| 6,152,935 A | 11/2000 | Kammerer et al. |
| 6,152,937 A | 11/2000 | Peterson et al. |
| 6,156,006 A | 12/2000 | Brosens et al. |
| 6,159,223 A | 12/2000 | Danks et al. |
| 6,171,321 B1 | 1/2001 | Gifford, III et al. |
| 6,183,486 B1 | 2/2001 | Snow et al. |
| 6,193,732 B1 | 2/2001 | Frantzen et al. |
| 6,200,329 B1 | 3/2001 | Fung et al. |
| 6,251,116 B1 | 6/2001 | Shennib et al. |
| 6,290,674 B1 | 9/2001 | Roue et al. |
| 6,293,952 B1 | 9/2001 | Brosens et al. |
| 6,293,961 B2 | 9/2001 | Schwartz et al. |
| 6,319,271 B1 | 11/2001 | Schwartz et al. |
| 6,328,727 B1 | 12/2001 | Frazier et al. |
| 6,348,059 B1 | 2/2002 | Hathaway et al. |
| 6,355,050 B1 | 3/2002 | Andreas et al. |
| 6,368,300 B1 | 4/2002 | Fallon et al. |
| 6,402,765 B1 | 6/2002 | Monassevitch et al. |
| 6,419,669 B1 | 7/2002 | Frazier et al. |
| 6,423,087 B1 | 7/2002 | Sawada |
| 6,428,550 B1 | 8/2002 | Vargas et al. |
| 6,494,889 B1 | 12/2002 | Fleischman et al. |
| 6,527,753 B2 | 3/2003 | Sekine et al. |
| 6,535,764 B2 | 3/2003 | Imran et al. |
| 6,543,456 B1 * | 4/2003 | Freeman ............... 128/898 |
| 6,569,173 B1 | 5/2003 | Blatter et al. |
| 6,572,629 B2 | 6/2003 | Kalloo et al. |
| 6,689,062 B1 | 2/2004 | Mesallum |
| 6,811,555 B1 | 11/2004 | Willis et al. |
| 6,918,871 B2 | 7/2005 | Schulze |
| 7,128,708 B2 | 10/2006 | Saadat et al. |
| 7,232,448 B2 | 6/2007 | Battles et al. |
| 7,273,451 B2 | 9/2007 | Sekine et al. |
| 7,351,202 B2 | 4/2008 | Long |
| 7,431,694 B2 | 10/2008 | Stefanchik et al. |
| 7,585,308 B2 | 9/2009 | Weisenburgh, II et al. |
| 7,591,828 B2 | 9/2009 | Ortiz |
| 7,608,086 B2 | 10/2009 | Tanaka et al. |
| 7,618,427 B2 | 11/2009 | Ortiz et al. |
| 7,637,919 B2 | 12/2009 | Ishikawa et al. |
| 7,654,951 B2 | 2/2010 | Ishikawa |
| 7,666,197 B2 | 2/2010 | Orban, III |
| 7,691,103 B2 | 4/2010 | Fernandez et al. |
| 7,708,748 B2 | 5/2010 | Weisenburgh, II et al. |
| 7,713,278 B2 | 5/2010 | Hess et al. |
| 7,725,214 B2 | 5/2010 | Diolaiti |
| 2001/0049497 A1 | 12/2001 | Kalloo et al. |
| 2002/0022851 A1 | 2/2002 | Kalloo et al. |
| 2003/0216613 A1 | 11/2003 | Suzuki et al. |
| 2003/0225312 A1 | 12/2003 | Suzuki et al. |
| 2004/0087985 A1 | 5/2004 | Loshakove et al. |
| 2004/0092975 A1 | 5/2004 | Loshakove et al. |
| 2004/0097801 A1 | 5/2004 | Mesallum |
| 2004/0225191 A1 | 11/2004 | Sekine et al. |
| 2004/0249367 A1 | 12/2004 | Saadat et al. |
| 2005/0004584 A1 | 1/2005 | Franco et al. |
| 2005/0101837 A1 | 5/2005 | Kalloo et al. |
| 2005/0107664 A1 | 5/2005 | Kalloo et al. |
| 2005/0277965 A1 | 12/2005 | Brenneman et al. |
| 2005/0277981 A1 | 12/2005 | Maahs et al. |
| 2006/0025654 A1 | 2/2006 | Suzuki et al. |
| 2006/0025788 A1 | 2/2006 | Loshakove et al. |
| 2006/0036267 A1 | 2/2006 | Saadat et al. |
| 2006/0100480 A1 | 5/2006 | Ewers et al. |
| 2006/0167482 A1 | 7/2006 | Swain et al. |
| 2006/0178560 A1 | 8/2006 | Saadat et al. |
| 2006/0200004 A1 | 9/2006 | Wilk |
| 2006/0211919 A1 | 9/2006 | Wilk |
| 2006/0212063 A1 | 9/2006 | Wilk |
| 2006/0229653 A1 | 10/2006 | Wilk |
| 2006/0237022 A1 | 10/2006 | Chen et al. |
| 2006/0237023 A1 | 10/2006 | Cox et al. |
| 2006/0241344 A1 | 10/2006 | Wilk |
| 2006/0241480 A1 | 10/2006 | Wilk |
| 2006/0241570 A1 | 10/2006 | Wilk |
| 2006/0241651 A1 | 10/2006 | Wilk |
| 2006/0241691 A1 | 10/2006 | Wilk |
| 2006/0252997 A1 | 11/2006 | Wilk |
| 2006/0253123 A1 | 11/2006 | Wilk |
| 2006/0258909 A1 | 11/2006 | Saadat et al. |
| 2006/0264986 A1 | 11/2006 | Park et al. |
| 2006/0287666 A1 | 12/2006 | Saadat et al. |
| 2006/0293701 A1 | 12/2006 | Ainsworth et al. |
| 2007/0004958 A1 | 1/2007 | Ohdaira |
| 2007/0051380 A1 | 3/2007 | Pasricha |

(56) References Cited

U.S. PATENT DOCUMENTS

| | | |
|---|---|---|
| 2007/0100375 A1 | 5/2007 | Mikkaichi et al. |
| 2007/0100376 A1 | 5/2007 | Mikkaichi et al. |
| 2007/0106313 A1 | 5/2007 | Golden et al. |
| 2007/0112362 A1 | 5/2007 | Mikkaichi et al. |
| 2007/0123840 A1 | 5/2007 | Cox |
| 2007/0163585 A1 | 7/2007 | Uesugi et al. |
| 2007/0163596 A1 | 7/2007 | Mikkaichi et al. |
| 2007/0163604 A1 | 7/2007 | Mikkaichi et al. |
| 2007/0167675 A1 | 7/2007 | Miyamoto et al. |
| 2007/0167676 A1 | 7/2007 | Miyamoto et al. |
| 2007/0167967 A1 | 7/2007 | Mikkaichi et al. |
| 2007/0173859 A1 | 7/2007 | Mikkaichi et al. |
| 2007/0173867 A1 | 7/2007 | Brenneman |
| 2007/0197864 A1 | 8/2007 | Dejima et al. |
| 2007/0198000 A1 | 8/2007 | Miyamoto et al. |
| 2007/0198033 A1 | 8/2007 | Kalloo et al. |
| 2007/0208360 A1 | 9/2007 | Demarais et al. |
| 2007/0213702 A1 | 9/2007 | Kogosaka et al. |
| 2007/0213749 A1 | 9/2007 | Kogosaka et al. |
| 2007/0213750 A1 | 9/2007 | Weadock |
| 2007/0219411 A1 | 9/2007 | Dejima et al. |
| 2007/0225734 A1 | 9/2007 | Bell et al. |
| 2007/0255100 A1 | 11/2007 | Barlow et al. |
| 2007/0255165 A1 | 11/2007 | Uesugi et al. |
| 2007/0255273 A1 | 11/2007 | Fernandez et al. |
| 2007/0255295 A1 | 11/2007 | Starkebaum et al. |
| 2007/0260214 A1 | 11/2007 | Mikkaichi et al. |
| 2007/0270629 A1 | 11/2007 | Charles |
| 2008/0015408 A1 | 1/2008 | Paolitto et al. |
| 2008/0021277 A1 | 1/2008 | Stefanchik |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkine |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065108 A1 | 3/2008 | Diolaiti |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0097489 A1 | 4/2008 | Goldfarb et al. |
| 2008/0114378 A1 | 5/2008 | Matsushita |
| 2008/0119868 A1 | 5/2008 | Sharp et al. |
| 2008/0125804 A1 | 5/2008 | Gostout |
| 2008/0154290 A1 | 6/2008 | Golden et al. |
| 2008/0161641 A1 | 7/2008 | Nakazato et al. |
| 2008/0171907 A1 | 7/2008 | Long et al. |
| 2008/0183039 A1 | 7/2008 | Long et al. |
| 2008/0200762 A1 | 8/2008 | Stokes et al. |
| 2008/0208161 A1 | 8/2008 | Kaji et al. |
| 2008/0208216 A1 | 8/2008 | Cerier |
| 2008/0228029 A1 | 9/2008 | Mikkaichi et al. |
| 2008/0228203 A1 | 9/2008 | Bell et al. |
| 2008/0249416 A1 | 10/2008 | Sato |
| 2008/0275297 A1 | 11/2008 | Bakos et al. |
| 2008/0287963 A1 | 11/2008 | Rogers et al. |
| 2008/0300618 A1 | 12/2008 | Gertner |
| 2008/0312502 A1 | 12/2008 | Swain et al. |
| 2009/0023985 A1 | 1/2009 | Ewers |
| 2009/0054728 A1 | 2/2009 | Trusty |
| 2009/0054761 A1 | 2/2009 | Voegele et al. |
| 2009/0182195 A1 | 7/2009 | Faller et al. |
| 2009/0221915 A1 | 9/2009 | Voegele et al. |
| 2009/0227828 A1 | 9/2009 | Swain et al. |
| 2009/0254105 A1 | 10/2009 | Thompson |
| 2009/0270912 A1 | 10/2009 | Surti |
| 2009/0276055 A1 | 11/2009 | Harris et al. |
| 2009/0281559 A1 | 11/2009 | Swain et al. |
| 2010/0010520 A1 | 1/2010 | Takahashi et al. |
| 2010/0036399 A1 | 2/2010 | Viola |
| 2010/0053514 A1 | 3/2010 | Chuang |
| 2010/0056861 A1 | 3/2010 | Spivey |
| 2010/0063521 A1 | 3/2010 | Manzo |
| 2010/0087842 A1 | 4/2010 | Heinrich et al. |
| 2010/0094319 A1 | 4/2010 | Heinrich et al. |
| 2010/0099947 A1 | 4/2010 | Sato et al. |
| 2010/0113872 A1 | 5/2010 | Asada et al. |
| 2010/0114124 A1 | 5/2010 | Kelleher et al. |
| 2010/0160729 A1 | 6/2010 | Smith et al. |
| 2010/0179510 A1 | 7/2010 | Fox et al. |
| 2010/0179540 A1 | 7/2010 | Marczyk et al. |
| 2010/0198232 A1 | 8/2010 | Diolaiti |
| 2011/0106109 A1 | 5/2011 | Surti et al. |

FOREIGN PATENT DOCUMENTS

| | | |
|---|---|---|
| EP | 1493391 A1 | 1/2005 |
| GB | 877903 | 9/1961 |
| WO | WO 98/02316 | 1/1998 |
| WO | WO 2006121855 | 11/2006 |
| WO | WO 2009/006444 | 1/2009 |
| WO | WO 2010/151382 | 12/2010 |
| WO | WO 2011/056445 | 5/2011 |

OTHER PUBLICATIONS

IPRP for PCT/US2011/032289 dated Oct. 16, 2012.
International Search Report and Written Opinion for PCT/US2010/053514 dated Dec. 6, 2010.
IPRP for PCT/US2010/053514 dated May 8, 2012.
International Search Report and Written Opinion for PCT/US2010/034690 dated Aug. 6, 2010.
IPRP for PCT/US2010/034690 dated Jan. 4, 2012.
Hagen, et al., Hybrid natural orifice transluminal endoscopic surgery (NOTES) for roux-en-Y gastric bypass: an experimental surgical study in human cadavers, 2008, pp. 918-924, vol. 40.
Fritscher-Ravens, EUS-Experimental and Evolving Techniques, 2006, pp. S95-S99, vol. 38.
Fritscher-Ravens, et al., Comparative study of NOTES alone vs. EUS-guided NOTES procedures, 2008, pp. 925-930, vol. 40.
Bories, et al., Transgastric endoscopic ultrasonography-guided biliary drainage: results of a pilot study, 2007, pp. 287-291, vol. 39.
Will, et al., Treatment of biliary obstruction in selected patients by endoscopic ultrasonography (EUS)-guided transluminal biliary drainage, 2007, pp. 292-295, vol. 39.
Office Action dated Sep. 5, 2012 U.S. Appl. No. 12/909,218 in related application.
Office Action dated Aug. 15, 2012 U.S. Appl. No. 12/779,378 in related application.
Office Action dated Feb. 6, 2013 U.S. Appl. No. 12/779,378 in related application.

* cited by examiner

SYSTEMS AND METHODS FOR CREATING ANASTOMOSES

CROSS-REFERENCE TO RELATED APPLICATIONS

This invention claims the benefit of U.S. Provisional Application Ser. No. 61/324,132 filed on Apr. 14, 2010, entitled "SYSTEMS AND METHODS FOR CREATING ANASTOMOSIS," the entire contents of which are incorporated herein by reference.

FIELD OF THE INVENTION

This invention relates to medical systems and methods for forming an anastomosis, and more particularly to forming an intestinal bypass anastomosis.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition.

More invasive approaches have been available which have yielded good results in many patients. These include surgical options such as bariatric surgery, bypass surgery or gastroplasty. However, these procedures carry high risks, and are therefore not appropriate for many patients. Even when carried out laparoscopically, these procedures are still considered major surgery due to the high risk and complication rates. One such method is forming a gastrojejunostomy, where a portion of the small intestine (e.g. the jejunum) is anastomosed to the stomach, thereby creating a bypass of a portion of the small intestine to create a malabsorptive effect and induce weight loss.

BRIEF SUMMARY OF THE INVENTION

The present invention provides medical systems and methods for forming an intestinal bypass anastomosis that is minimally invasive with reduced complications. According to one embodiment, a method of forming an anastomosis between a first section and a second section of the digestive tract is provided in accordance with the teachings of the present invention. As one example, the anastomosis may create a passageway directly from the stomach to the small intestine to bypass a portion of the small intestine (e.g. the jejunum, thereby forming a gastrojejunostomy), which is commonly done to treat obesity, diabetes, cancer and other diseases or defects. In one embodiment, the method includes forming a first opening in the first section and forming a second opening in the first section. A proximal portion of the second section is moved to a position adjacent the first opening, and a distal portion of the second section is moved to a position adjacent the second opening. In this manner, an intermediate portion of the second section extends along the first section and an anastomosis can then be formed between the first section and the second section.

According to more detailed aspects, the method may further include the step of attaching the proximal portion of the second section to the first section adjacent the first opening. The proximal portion may be attached through application of any one of a tack, a suture or a clip to the first and second sections. Similarly, the distal portion of the second section may be attached to the first section adjacent the second opening in a similar manner. Alternatively, a first tissue anchor may be deployed within the proximal portion of the second section, and a second tissue anchor may be deployed within the distal portion of the second section. The tissue anchors may be tensioned to position the proximal and distal portions adjacent the first and second openings, respectively, and position the intermediate portion of the second section alongside the first section.

According to further detailed aspects, the step of moving a proximal portion of the second section includes moving the proximal portion through the first opening to form a first loop in the second section, and the step of moving the distal portion includes moving the distal portion through the second opening to form a second loop in the second section. A grasping device such as forceps may be employed through an endoscope to grasp and move the proximal and distal portions, or tissue anchors may be deployed within the proximal and distal portions and tensioned to move the proximal and distal portions through the first and second openings. The first and second loops are preferably positioned on an interior side of the first section, while the intermediate portion of the second section is positioned on an exterior side of the first section.

According to still further detailed aspects, the method may also include the step of maintaining the position of the first and second loops on the interior side of the first section. Maintaining the position of the loops may be accomplished by applying at least one a tack, a suture or a clip to the first and second loops in the second section. Tissue anchors placed within the first and second loops may also be used to maintain the position of the first and second loops through tensioning of the tissue anchor. Alternatively, an elongate member, such as a suture, a wire guide or a catheter may be passed through the first and second loops and tensioned to maintain the position of the loops. For example, a first elongate member may be passed through the first loop and a second elongate member may be passed through the second loop, which then can be independently tensioned to maintain the position of the first and second loops.

Upon completing the anastomosis, the first and second loops may be repositioned on the exterior side of the first section, and the first and second openings in the first section may be closed. An anastomotic device may be placed within the anastomosis, for example an anastomotic ring, anastomosis clip, sutures and related devices may be used to maintain the anastomosis. Generally, the step of forming an anastomosis includes forming a third opening in the first section and a fourth opening in the second section, and placing an anastomotic device within the third and fourth openings to approximate the first and second sections.

According to another embodiment, a system for forming an anastomosis between bodily lumens is provided. The system generally includes an endoscope, an elongated cutting device, an elongated grasping device, and an elongated needle having a needle lumen containing two tissue fixation devices. The endoscope includes two working channels through which elongate medical instruments may be employed. The two tissue fixation devices are suitable for fixing two portions of a bodily lumen in a manner such as described above, and may include tacks, clips, tissue anchors and the like, or may simply include an elongate member (e.g. suture, wire guide or catheter) that is looped through the bodily lumen to fix or otherwise hold the positions of the two portions for forming an anastomosis. The cutting device and grasping device are structured for use with the first working channel and the elongated needle is structured for use with the second working channel. The grasping device is independently operable from the needle and tissue fixation devices such that the grasping device may be tensioned proximally while the needle is advanced distally, and such that the tissue fixation device may be tensioned proximally while the cutting device is advanced distally.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Figure 1:
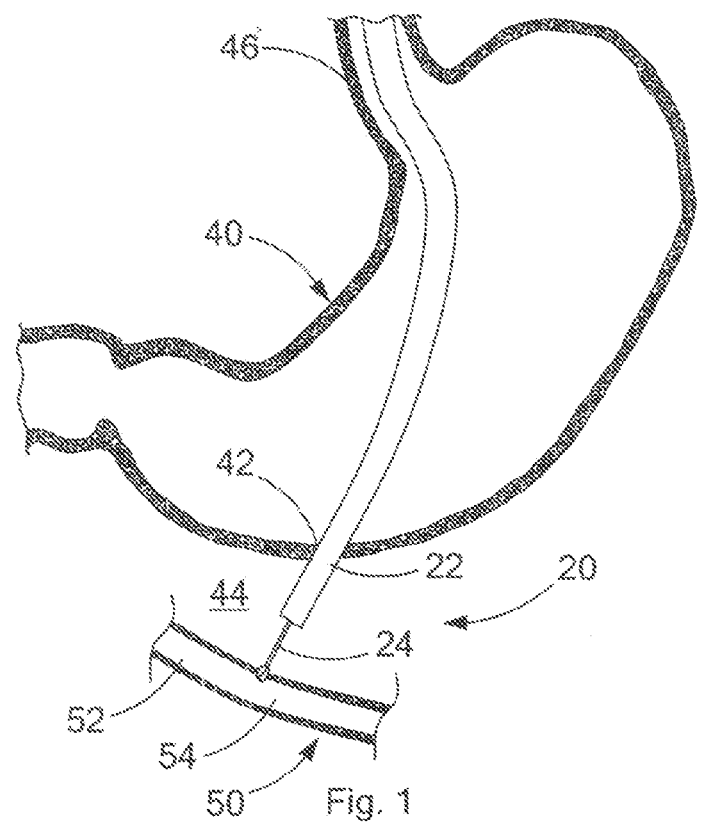
FIG. 1 depicts a schematic view, partially in cross-section, depicting a system and method step for forming an anastomosis.

Turning now to the figures, FIG. 1 depicts portions of a system 20 and method for forming an anastomosis between a first section 40 of the digestive tract and a second section 50 of the digestive tract. In the depicted embodiments, the first section 40 is generally depicted as the stomach, while the second section 50 has been depicted as a portion of the small intestine, for example, to perform a gastrojejunostomy to bypass the jejunum 52 or other portion of the small intestine 50. Accordingly, as used herein the terms "stomach" and "small intestine" are interchangeable with "first section" and "second section" of the digestive tract. Moreover, it will be recognized by those skilled in the art that the terms "first section" and "second section" of the digestive tract may include any portion of the digestive tract from the mouth to the anus, as an anastomosis may also be formed between the esophagus and stomach, the stomach and large intestine, the small intestine and other portions of the small intestine or large intestine, and the small and large intestines with the colon.

The medical system 20 generally includes an endoscope 22 and a variety of instruments and devices that can work through the endoscope 22, or work alongside and in parallel with the endoscope 22. Preferably, the endoscope 22 has two working or auxiliary channels such that two instruments may be employed through the endoscope 22. As will be described further below, the system 20 preferably includes an elongated cutting device (e.g. needle knife 29), an elongated grasping device (e.g. forceps 24), and an elongated needle (e.g. 28) having a needle lumen containing two tissue fixation devices suitable for fixing two portions of a bodily lumen in a manner such as described below, and may include tacks (e.g. 26), clips, tissue anchors (e.g. 36) and the like, or may simply include an elongate member (e.g. suture, wire guide or catheter) that is looped through the bodily lumen to fix or otherwise hold the positions of the two portions for forming an anastomosis.

However, a single channel endoscope may also be employed and the medical instruments (which will be described further hereinbelow) may be employed alongside the endoscope 22. Similarly, other elongate visualization devices, such as catheter-based fiber optic systems, or even visualization techniques such as fluoroscopy, ultrasound or the like, may be used to monitor the position of the instruments for performing the steps described herein.

As shown in FIG. 1, the endoscope 22 is passed through the mouth and esophagus 46 and into the stomach 40. The system 20 is utilized to form a first opening 42 in the stomach 40 (i.e. in the first section). A needle knife 29 (shown in FIG. 10, not depicted in FIG. 1) or other cutting device, preferably an electrosurgical cutting device, may be employed through or alongside the endoscope 22 to form the first opening 42. A balloon dilator or other dilation device (not shown) may also be used to enlarge the first opening 42 as desired. The endoscope 22 may then be passed through the first opening 42 to the exterior of the stomach 40, namely into the peritoneal cavity 44. A grasping device 24 may be used to engage a proximal portion 54 of the intestine 50. It will be recognized that various grasping devices 24 may be used, for example hooks, wire graspers, clamps, piercing or screw tip devices and the like, and forceps 24 have been depicted in FIG. 1.

Figure 2:
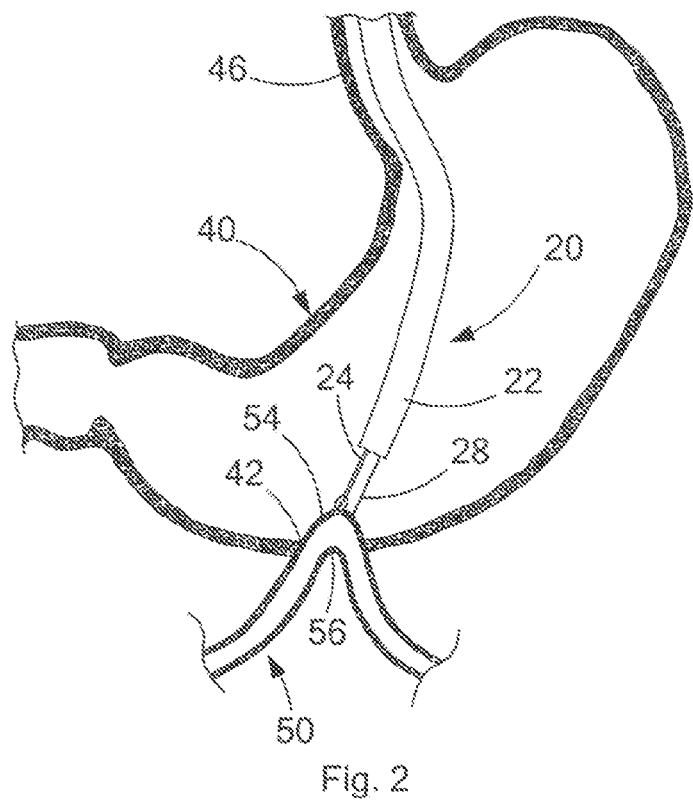
FIG. 2 depicts a schematic view, partially in cross-section, depicting a system and method step for forming an anastomosis.

As shown in FIG. 2, the medical system 20, and namely the endoscope 22 and/or grasping device 24 may be retracted proximally to move the proximal portion 54 of the intestine 50 to a position adjacent the first opening 42. Preferably, the proximal portion 54 is pulled through the first opening 42 thereby forming a first loop 56 in the intestine 50.

Figure 3:
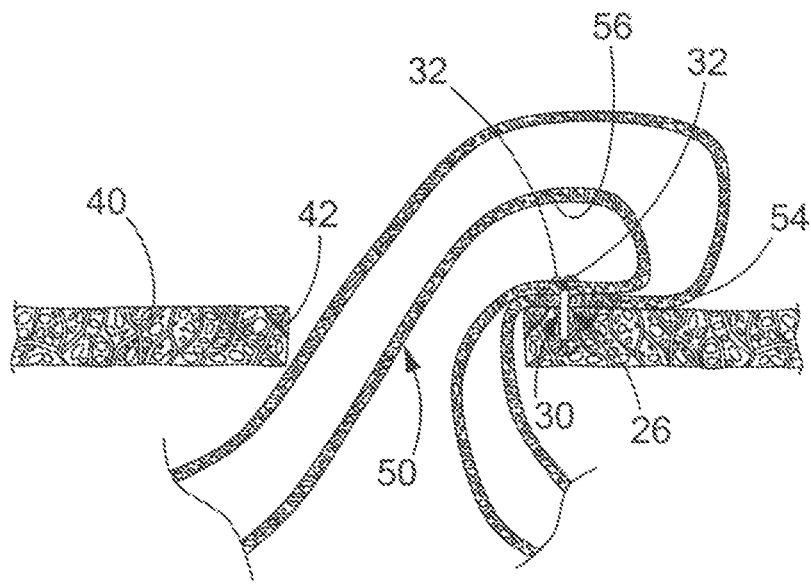
FIG. 3 depicts a schematic view, partially in cross-section, depicting a system and method step for forming an anastomosis.

As best seen in FIG. 3, the proximal portion 54 in the first loop 56 formed by the intestine 50 is maintained in this position on the interior of the stomach 40 by attaching the proximal portion 54 to the wall of the stomach 40 utilizing a tack 26, which may be delivered through a needle 28 (FIG. 2). Exemplary tacks and delivery devices are shown in U.S. patent application Ser. No. 12/428,226 filed Apr. 22, 2009, U.S. application Ser. No. 12/632,281 filed Dec. 7, 2009, U.S. application Ser. No. 12/608,621 filed Oct. 29, 2009 and U.S. application Ser. No. 12/632,300 filed Dec. 7, 2009, and U.S. application Ser. No. 12/632,208 filed Dec. 15, 2009, and the contents of all these applications are incorporated herein by reference in their entirety. Generally, the tack 26 depicted in FIG. 3 includes a central member 30 having a plurality of flexible hook-shaped elements 32 (e.g. formed of nitinol). The hook-shaped elements 32 are preferably delivered in a linear state and, upon ejection from the needle 28, retroflex into their hook shape as shown in FIG. 3. It will also be recognized that numerous other tissue fixation devices and methods may be employed including suturing techniques, staples and clips. Exemplary endoscopic suturing techniques and devices are disclosed in U.S. 61/174,583 filed May 1, 2009, and U.S. Ser. No. 12/348,180 filed Jan. 2, 2009. Exemplary clips are disclosed in Ser. No. 12/638,190 filed Dec. 15, 2009, and U.S. 61/289,297 filed Dec. 22, 2009. The disclosures of all the above-mentioned patent applications are incorporated herein by reference in their entirety.

Figure 4:
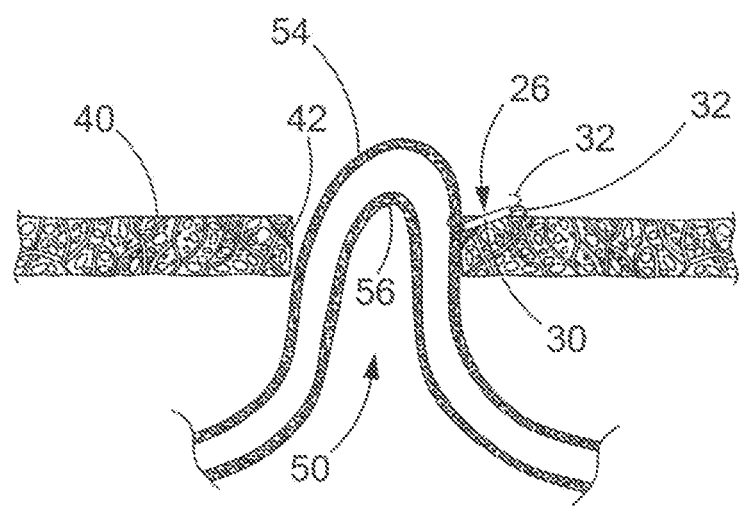
FIG. 4 is also a schematic view, partially in cross-section, depicting an alternate method step to that shown in FIG. 3.

As shown in FIG. 3, the first loop 56 of the proximal portion 54 is positioned laterally along the wall of the stomach 40 while the tack 26 is passed through opposing layers of the intestine 50. Alternatively, as shown in FIG. 4, the grasping device 24 may be used to hold the proximal portion 54 and loop 56 in place while a tack 26 is deployed in an angular fashion through the wall of the stomach 40 adjacent the opening 42 and through only one layer of the intestine 50.

Figure 5:
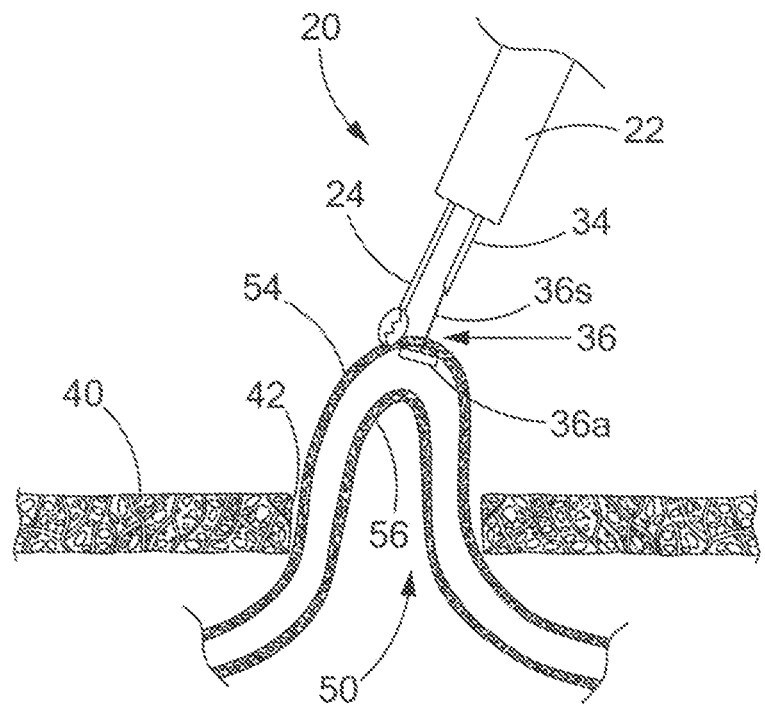
FIG. 5 is also a schematic view, partially in cross-section, depicting an alternate method step to that of FIG. 3.
Figure 6:
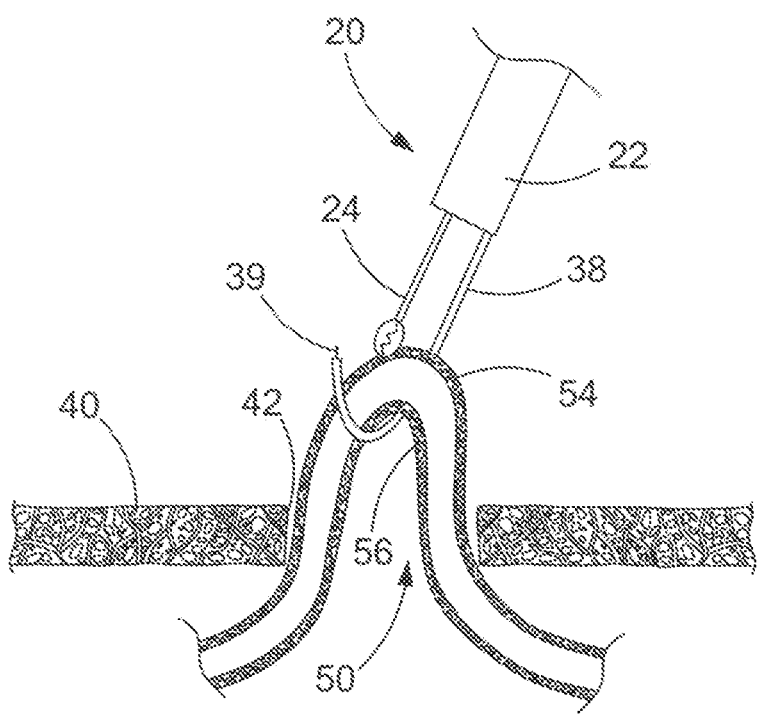
FIG. 6 is also a schematic view, partially in cross-section, depicting an alternate method step to that of FIG. 3.

Other alternate methods for fixing or maintaining the position of the first loop 56 are shown in FIGS. 5 and 6. For example, the grasping device 24 may be utilized to engage the proximal portion 54 of the intestine 50 and pull it through the first opening 42. Then, a needle 34 having a tissue anchor 36 may be advanced through the second working channel of the endoscope 22 to deliver the tissue anchor 36 within the proximal portion 54 of the intestine 50. Generally, the tissue anchor 36 includes a cross bar or anchoring member 36a connected to a suture 36s which extends through the needle 34. Alternatively, the suture 36s may extend alongside the needle, or even alongside the endoscope 22. The suture 36s may then be tensioned to maintain the position of the proximal portion 54 and loop 56 on the interior side of the stomach 40. It will also be recognized that the method may modified to eliminate the grasping device 24, wherein the tissue anchor 36 is used to engage and move the proximal portion 54 of the intestine 50. For example, the tissue anchor 36 may be delivered into the intestine 50 while still in its normal position on the exterior of the stomach 40 (i.e. within the peritoneal cavity 44), and then the suture 36s tensioned and moved proximally to draw the proximal portion 54 of the intestine 53 through the first opening 42 to form the first loop 56. Exemplary tissue anchors and related devices are disclosed in U.S. Ser. No. 11/946,565 filed Nov. 28, 2007, U.S. Ser. No. 12/191,277 filed Aug. 13, 2008, and Ser. No. 12/630,395 filed Dec. 3, 2009, the contents of all the above-mentioned applications are incorporated herein by reference in their entirety.

In an alternate embodiment shown in FIG. 6, once the grasping device 24 has engaged and moved the proximal portion 54 of the intestine 50 through the opening 42 to form the first loop 56, an elongate device may be deployed through the loop 56, here depicted as a catheter 38 having a curved distal end for passing a suture 39 through the first loop 56. The grasping device 24 may release the proximal portion 54 of the intestine 50 and grasp the distal end of the suture 39 (or other elongate member), to allow the elongate member 39 to be looped through the first loop 56 of the intestine 50 and brought within the control of the user of the medical system 20. An instrument delivered alongside the endoscope 22 may alternatively be used to grasp the suture 39, or the catheter 38 itself may have a catch feature that allows recapture of the suture 39. It will be recognized that the hook-shaped catheter 38 or other hook-shaped or elongate member could alone be used to engage and maintain the position of the loop 56. Likewise, other elongate members such as the suture 39, wire guides (preferably steerable wire guides), catheters (preferably steerable catheters) or the like may be passed through the first loop 56 of the intestine 50 and back through the stomach 40 and esophagus 46, where both ends of the elongate member may be operated by the user. In this manner, tension on the elongate member can be used to maintain the position of the first loop 56.

Figure 7:
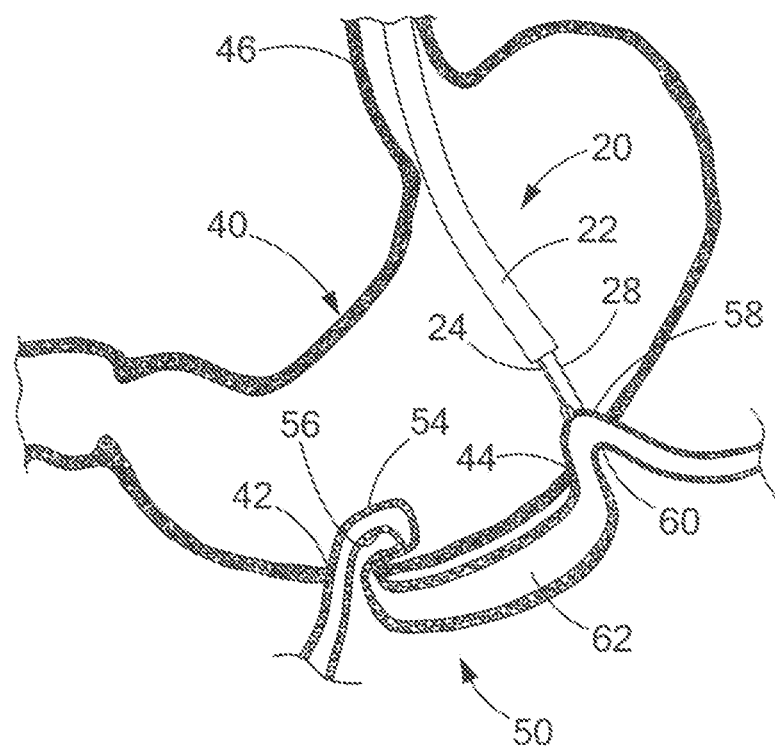
FIG. 7 depicts a schematic view, partially in cross-section, depicting a system and method step for forming an anastomosis.

Turning now to FIG. 7, similar steps to those describe above in FIGS. 1-6 are performed again with regard to a distal portion 58 of the intestine 50. The medical system 20 is again used to form a second opening 44 in the stomach 40 at a position spaced away from the first opening 42. The medical system 20 is passed through the opening 44 and the grasping device 24 is used to engage the distal portion 58 of the intestine 50. The medial system 20, endoscope 22 and/or grasping device 24 are retracted proximally through the second opening 44 to form a second loop 60 of the intestine 50 on the interior side of the stomach 40. The position of the second loop 60 and distal portion 58 of the intestine 50 is maintained through any of the aforementioned methods and devices, for example using a needle 28 to deliver a tack 26 as shown in FIG. 8.

Figure 8:
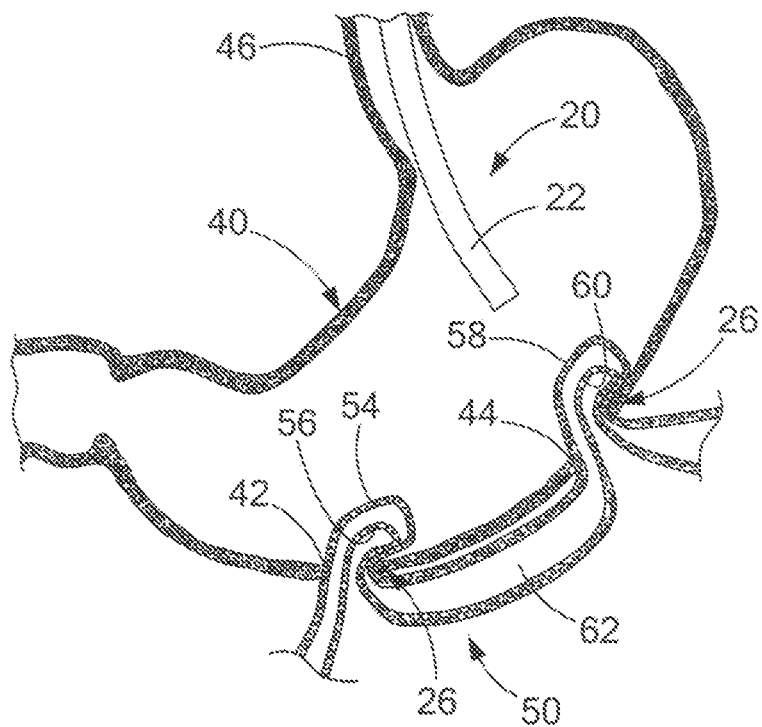
FIG. 8 depicts a schematic view, partially in cross-section, depicting a system and method step for forming an anastomosis.
Figure 9:
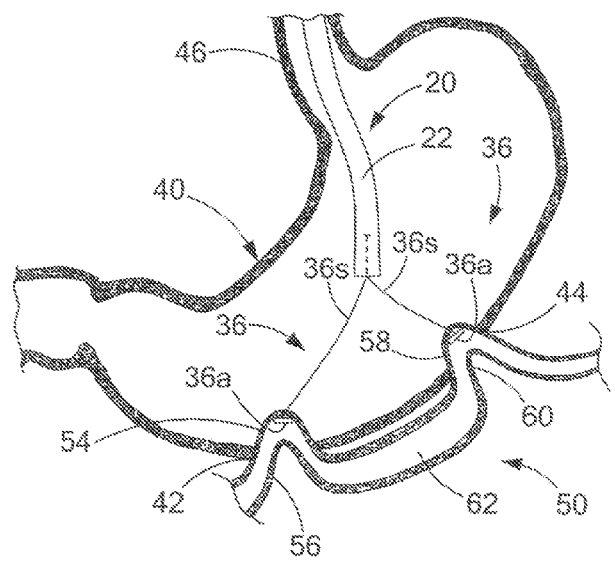
FIG. 9 depicts a schematic view, partially in cross-section, depicting a system and method step for forming an anastomosis.

Accordingly, and as best seen in FIG. 8, through grasping and positioning a proximal portion 54 and a distal portion 58 of the intestine 50 adjacent first and second openings 42, 44 in the stomach 40, an intermediate portion 62 of the intestine 50 extends along the exterior of the stomach 40 thus providing an ideal position for forming an anastomosis. Similarly, as shown in FIG. 9, the tissue anchors 36 may be used to form or simply maintain the position of the loops 56, 60 of the proximal and distal portions 54, 58 of the intestine 50. Notably, in the embodiment of FIG. 9 the sutures 36s of the anchors 36 may be tensioned to control the approximation of intermediate portion 62 of the intestine 50 to the exterior wall of the stomach 40. Tensioning and adjustment of the intestine 50 can occur throughout the procedure.

Figure 10:
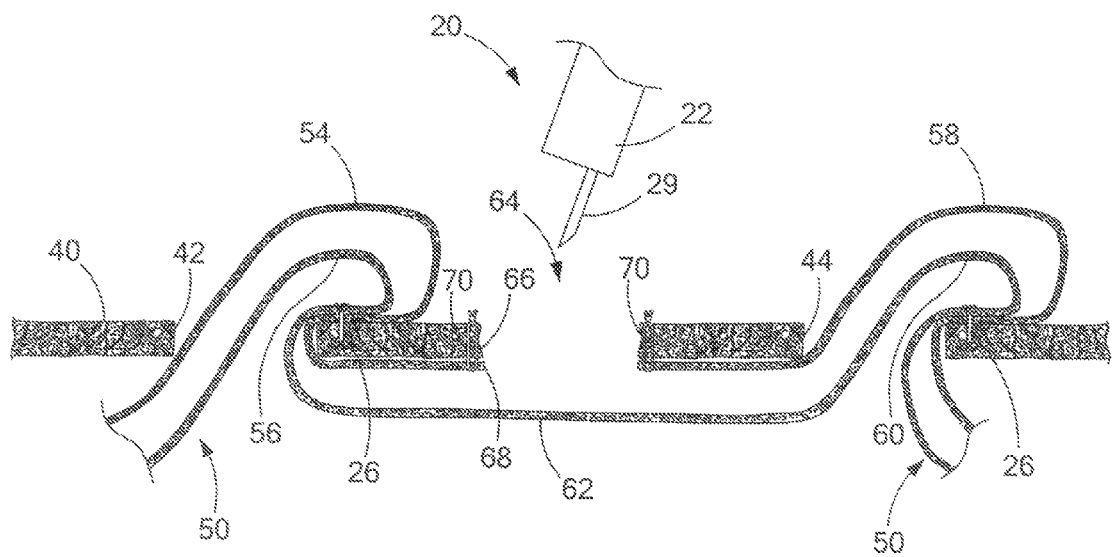
FIG. 10 depicts a schematic view, partially in cross-section, depicting a system and method step for forming an anastomosis.
Figure 11:
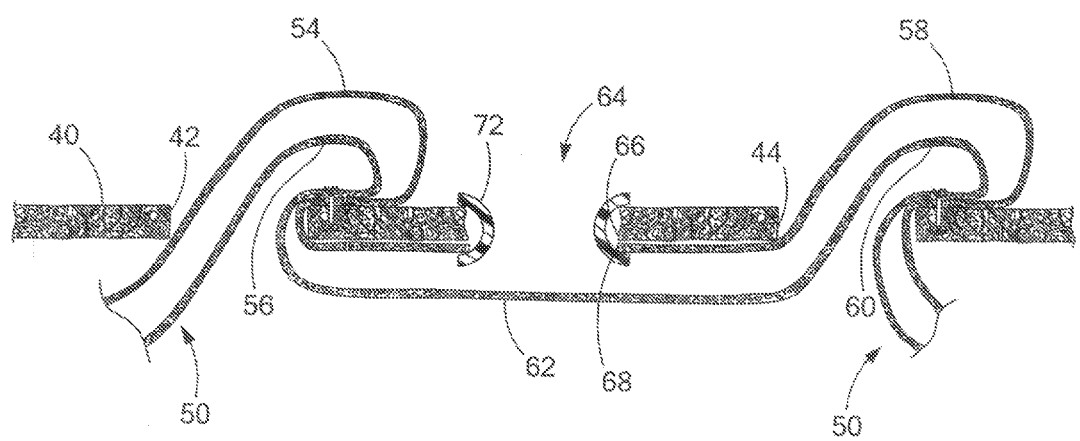
FIG. 11 depicts a schematic view, partially in cross-section, depicting an alternate system and method step to that disclosed in FIG. 10.
Figure 12:
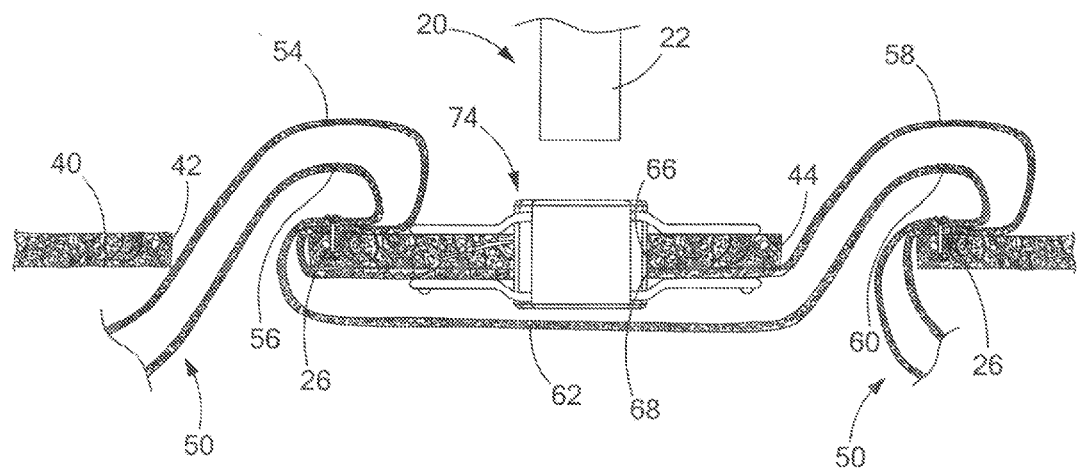
FIG. 12 depicts a schematic view, partially in cross-section, depicting an alternate system and method step to that disclosed in FIG. 10.

Turning now to FIG. 10, an anastomosis 64 is shown formed between the stomach 40 and intestine 50, i.e. between the first section of the digestive tract and the second section of the digestive tract. That is, a third opening 66 is formed in the wall of the stomach 40 and a fourth opening 68 is formed in one wall of the intestine 50, and in particular within the intermediate portion 62 of the intestine 50. The openings 66, 68 may be formed utilizing a needle knife 29 or other cutting tool such as those described above in connection with the first and second openings 42, 44 in the stomach 40. The walls of the intestine 50 and stomach 40 may be approximated and held in place using suture 70 or another anastomotic device using suture 70 or other anastomotic devices. As shown in FIG. 11, such other anastomotic devices include an anastomotic ring 72 which is formed of a polymer and has an annular shape, preferably with a cross-section in a U-shape or a C-shape. Similarly, FIG. 12 depicts an anastomotic clip 74 being deployed to form the anastomosis 64. Exemplary anastomotic clips are disclosed in U.S. Application Nos. 61/227, 848 filed Jun. 26, 2009 and 61/257,654 filed Nov. 3, 2009, the disclosures of which are incorporated herein by reference in their entirety.

Figure 13:
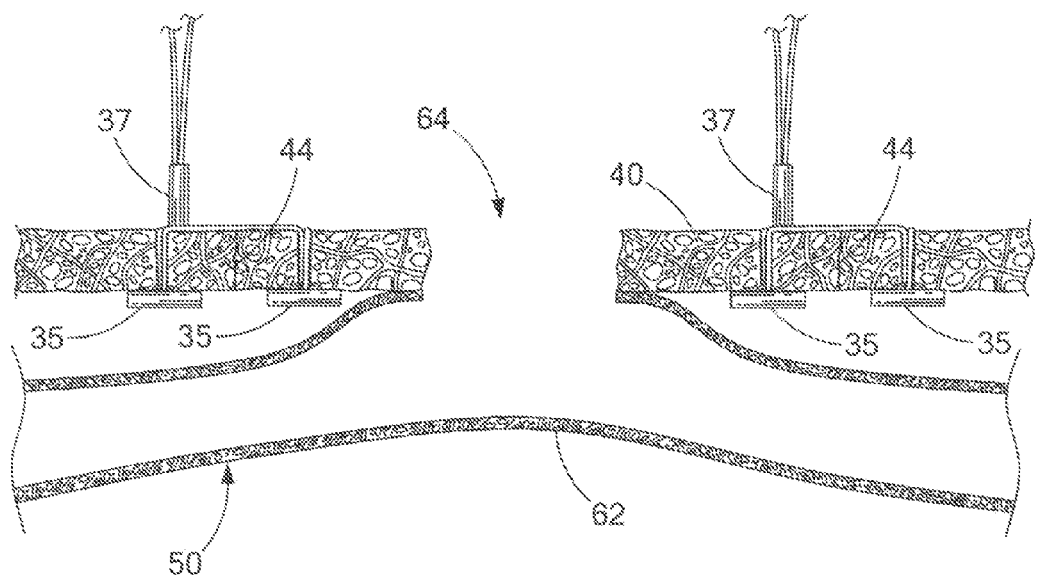
FIG. 13 depicts a schematic view, partially in cross-section, depicting a system and method step for forming an anastomosis.

Turning now to FIG. 13, with the anastomosis 64 formed between the stomach 40 and intestine 50, the proximal and distal portions 54, 58 of the intestine 50, including the loops 56, 60, may be detached from the wall of the stomach 40, and repositioned (e.g. using the grasping device 24) or otherwise released such that they are positioned on the exterior of the stomach 40 and in the peritoneal cavity 44. The first and second openings 42, 44 in the stomach 40 may then be closed. Many known or hereinafter developed methods and devices for closing perforations in the stomach 40 may be employed, including suturing devices and techniques, tissue anchors, staples, clips, tacks and the like. For example, exemplary methods and devices are disclosed in the above-mentioned references regarding tissue anchors, and further exemplary devices and systems are disclosed in U.S. Patent Application 61/166,361 filed Apr. 3, 2009, Ser. No. 12/236,236 filed Sep. 23, 2007, Ser. No. 12/191,285 filed Aug. 13, 2008, Ser. No. 12/348,180 filed Jan. 2, 2009, Ser. No. 12/557,232 filed Sep. 20, 2009, 61/256,619 filed Oct. 30, 2009 and Ser. No. 12/548,868 filed Aug. 27, 2009, all the above-mentioned applications are incorporated herein by reference in their entirety. FIG. 13 depicts a plurality of purse string tissue anchors 35 placed through the stomach 40 having a single suture slidably attached thereto, which can be tensioned to close the first and second openings 42, 44. The sutures are maintained in a tension state utilizing a suture lock 37. Exemplary suture locks are disclosed in U.S. patent application Ser. Nos. 12/191,001 and filed Aug. 13, 2008, 12/125,525 filed May 22, 2008.

Accordingly, it will be recognized by those skilled in the art that a minimally invasive method for bypassing a portion of the digestive tract (e.g., the small intestine) is provided to create a malabsorptive effect and induce weight loss. The complications and other problems utilizing conventional surgical or laparoscopic techniques are minimized or avoided, while retaining control over placement of the anastomosis and hence the bypassed portions of the small intestine.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of forming an anastomosis between a first section of the digestive tract and second section of the digestive tract, the method comprising the steps of:
    forming a first opening in the first section;
    forming a second opening in the first section;
    moving a proximal portion of the second section to a position adjacent the first opening;
    moving a distal portion of the second section to a position adjacent the second opening, whereby an intermediate portion of the second section extends along the first section between the first and second openings; and
    forming an anastomosis between the first section and the intermediate portion of the second section.

2. The method of claim 1, further comprising the step of attaching the proximal portion of the second section to the first section adjacent the first opening.

3. The method of claim 2, wherein the step of attaching includes applying at least one of a tack, a suture, and a clip to the first and second sections.

4. The method of claim 2, further comprising the step of attaching the distal portion of the second section to the first section adjacent the second opening.

5. The method of claim 4, wherein the steps of attaching includes applying at least one of a tack, a suture, and a clip to the first and second sections.

6. The method of claim 1, further comprising the steps of deploying a first tissue anchor within the proximal portion of the second section, and deploying a second tissue anchor within the distal portion of the second section.

7. The method of claim 6, wherein the first and second tissue anchors each include an engagement member connect to suture, and further comprising the step of tensioning the sutures to position the intermediate portion of the second section alongside the first section.

8. The method of claim 1, further comprising the step of closing the first and second openings in the first section.

9. The method of claim 1, further comprising the step of placing an anastomotic device within the anastomosis.

10. The method of claim 1, wherein the step of forming an anastomosis includes forming a third opening in the first section and a fourth opening in the second section, and placing an anastomotic device within the third and fourth openings to approximate the first and second sections.

11. A method of forming an anastomosis between a first section of the digestive tract and second section of the digestive tract, the method comprising the steps of:
    forming a first opening in the first section;
    forming a second opening in the first section;
    moving a proximal portion of the second section to a position adjacent the first opening and through the first opening to form a first loop in the second section; and
    moving a distal portion of the second section to a position adjacent the second opening and through the second opening to form a second loop in the second section; and
    forming an anastomosis between the first section and the second section.

12. The method of claim 11, wherein the moving steps include deploying a first tissue anchor within the proximal portion of the second section and deploying a second tissue anchor within the distal portion of the second section, and tensioning the first and second tissue anchors to move the proximal and distal portions.

13. The method of claim 11, wherein the first and second loops are positioned on an interior side of the first section, and the intermediate portion of the second section is positioned on an exterior side of the first section.

14. The method of claim 13, further comprising the step of maintaining the position of the first and second loops on the interior side of the first section.

15. The method of claim 14, wherein the step of maintaining the position of the first loop includes applying at least one of a tack, a suture, and a clip to the first loop and second section, and wherein the step of maintaining the position of the second loop includes applying at least one of a tack, a suture, and a clip to the second loop and second section.

16. The method of claim 14, wherein the step of maintaining the position of the first and second loops includes placing a tissue anchor within the first and second loops, and applying tension on the tissue anchors.

17. The method of claim 14, wherein the step of maintaining the position of the first and second loops includes passing an elongate member through both the first and second loops and applying tension on the elongate member.

18. The method of claim 14, wherein the step of maintaining the position of the first loop includes passing a first elongate member through the first loop and applying tension to the first elongate member, and includes passing a second elongate member through the second loop and applying tension to the second elongate member.

19. The method of claim 11, further comprising the step of repositioning the first and second loops of the proximal and distal portions of the second section on the exterior side of the first section.

\* \* \* \* \*